US010940251B2

(12) United States Patent
Hansen

(10) Patent No.: US 10,940,251 B2
(45) Date of Patent: Mar. 9, 2021

(54) MECHANICAL GAUGE FOR ESTIMATING INDUCTANCE CHANGES IN RESONANT POWER TRANSFER SYSTEMS WITH FLEXIBLE COILS FOR USE WITH IMPLANTED MEDICAL DEVICES

(71) Applicant: TC1 LLC, St. Paul, MN (US)

(72) Inventor: John Freddy Hansen, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 90 days.

(21) Appl. No.: 16/357,863

(22) Filed: Mar. 19, 2019

(65) Prior Publication Data
US 2019/0290819 A1    Sep. 26, 2019

Related U.S. Application Data

(60) Provisional application No. 62/645,594, filed on Mar. 20, 2018.

(51) Int. Cl.
| | | |
|---|---|---|
| *A61M 1/12* | (2006.01) | |
| *H02J 7/00* | (2006.01) | |
| *H02J 50/00* | (2016.01) | |
| *A61M 1/10* | (2006.01) | |
| *H02J 7/02* | (2016.01) | |
| *A61N 1/362* | (2006.01) | |
| *H02J 50/12* | (2016.01) | |
| *A61N 1/378* | (2006.01) | |

(Continued)

(52) U.S. Cl.
CPC ............ *A61M 1/127* (2013.01); *A61M 1/122* (2014.02); *H02J 7/00* (2013.01); *H02J 50/00* (2016.02); *A61M 1/1086* (2013.01); *A61M 2205/82* (2013.01); *A61M 2205/8243* (2013.01); *A61N 1/3627* (2013.01); *A61N 1/3787* (2013.01); *H02J 7/025* (2013.01); *H02J 50/12* (2016.02)

(58) Field of Classification Search
None
See application file for complete search history.

(56) References Cited

U.S. PATENT DOCUMENTS

| | | |
|---|---|---|
| 5,695,471 A | 12/1997 | Wampler |
| 5,708,346 A | 1/1998 | Schoeb |
| 5,888,242 A | 3/1999 | Antaki et al. |

(Continued)

FOREIGN PATENT DOCUMENTS

| | | |
|---|---|---|
| WO | 2008106717 A1 | 9/2008 |
| WO | 2017021846 A1 | 2/2017 |

*Primary Examiner* — Brian T Gedeon
(74) *Attorney, Agent, or Firm* — Kilpatrick Townsend & Stockton LLP

(57) ABSTRACT

Systems and devices for improving wireless power transmission are disclosed herein. The system can include an implantable medical device that can include an energy storage component and a secondary coil electrically coupled to the energy storage component. The system can include a charging device. The charging device can include a flexible housing defining an internal volume, a resonant circuit, a plurality of sensors coupled to the primary coil, and processor. The resonant circuit can include a deformable primary coil located within the internal volume of the housing. The processor can determine a deformation of the primary coil based on at least one signal received from at least one of the plurality of sensors.

33 Claims, 7 Drawing Sheets

(51) Int. Cl.
*H04B 5/00* (2006.01)
*H02J 50/80* (2016.01)

(56) References Cited

U.S. PATENT DOCUMENTS

| | | | |
|---|---|---|---|
| 6,053,705 A | 4/2000 | Schoeb et al. | |
| 6,071,093 A | 6/2000 | Hart | |
| 6,100,618 A | 8/2000 | Schoeb et al. | |
| 6,116,862 A | 9/2000 | Rau et al. | |
| 6,186,665 B1 | 2/2001 | Maher et al. | |
| 6,222,290 B1 | 4/2001 | Schoeb et al. | |
| 6,234,772 B1 | 5/2001 | Wampler et al. | |
| 6,249,067 B1 | 6/2001 | Schob et al. | |
| 6,264,635 B1 | 7/2001 | Wampler et al. | |
| 6,278,251 B1 | 8/2001 | Schob | |
| 6,351,048 B1 | 2/2002 | Schob et al. | |
| 6,355,998 B1 | 3/2002 | Schoeb et al. | |
| 6,634,224 B1 | 10/2003 | Schob et al. | |
| 6,688,861 B2 | 2/2004 | Wampler | |
| 6,879,074 B2 | 4/2005 | Amrhein et al. | |
| 6,991,595 B2 | 1/2006 | Burke et al. | |
| 7,112,903 B1 | 9/2006 | Schob | |
| 7,699,586 B2 | 4/2010 | LaRose et al. | |
| 7,976,271 B2 | 7/2011 | LaRose et al. | |
| 7,997,854 B2 | 8/2011 | LaRose et al. | |
| 8,007,254 B2 | 8/2011 | LaRose et al. | |
| 8,152,493 B2 | 4/2012 | LaRose et al. | |
| 8,323,174 B2 | 12/2012 | Jeevanandam et al. | |
| 8,449,444 B2 | 5/2013 | Poirier | |
| 8,506,471 B2 | 8/2013 | Bourque | |
| 8,562,508 B2 | 10/2013 | Dague et al. | |
| 8,597,350 B2 | 12/2013 | Rudser et al. | |
| 8,652,024 B1 | 2/2014 | Yanai et al. | |
| 8,657,733 B2 | 2/2014 | Ayre et al. | |
| 8,668,473 B2 | 3/2014 | LaRose et al. | |
| 9,805,863 B2 | 10/2017 | Hansen et al. | |
| 2005/0071001 A1 | 3/2005 | Jarvik | |
| 2007/0078293 A1 | 4/2007 | Shambaugh, Jr. et al. | |
| 2008/0021394 A1 | 1/2008 | LaRose et al. | |
| 2009/0203957 A1 | 8/2009 | LaRose et al. | |
| 2009/0261828 A1* | 10/2009 | Nordmeyer-Massner | G01R 33/34046 324/318 |
| 2012/0046514 A1 | 2/2012 | Bourque | |
| 2012/0095281 A1 | 4/2012 | Reichenbach et al. | |
| 2013/0096364 A1 | 4/2013 | Reichenbach et al. | |
| 2013/0105115 A1* | 5/2013 | Kallmyer | H05K 7/20 165/76 |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0314047 A1 | 11/2013 | Eagle et al. | |
| 2014/0028110 A1 | 1/2014 | Petersen et al. | |
| 2016/0072297 A1* | 3/2016 | Fine | H02J 50/12 307/104 |
| 2016/0233023 A1 | 8/2016 | Zilbershlag | |
| 2017/0063143 A1 | 3/2017 | Hoarau et al. | |
| 2017/0353061 A1* | 12/2017 | Maniktala | H02J 50/90 |
| 2019/0225909 A1 | 7/2019 | Miller et al. | |

\* cited by examiner

MECHANICAL GAUGE FOR ESTIMATING INDUCTANCE CHANGES IN RESONANT POWER TRANSFER SYSTEMS WITH FLEXIBLE COILS FOR USE WITH IMPLANTED MEDICAL DEVICES

CROSS REFERENCE TO RELATED APPLICATIONS

The present application claims the benefit under 35 USC § 119(e) of U.S. Provisional Appln. No. 62/645,594 filed Mar. 20, 2018; the full disclosure which is incorporated herein by reference in its entirety for all purposes.

BACKGROUND

This application relates generally to medical devices, and more specifically relates to methods and devices for improved charging of wireless medical devices.

Implanted medical devices frequently utilize electrical power to enable their operation. This electrical power is frequently provided through the use of a driveline that extends through the skin to physically connect the Implanted medical device to an external power source or alternatively through the use of features that allow wireless charging of the Implanted medical device. Whether power is provided via a wire or wirelessly, the providing of power to the implanted medical device creates many challenges for patients and providers.

One type of implantable medical device are ventricular assist devices, known as VADs. VADs are implantable blood pumps that are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

While a VAD can greatly improve a patient's life, use of a VAD can provide challenges to the patient and provider. These challenges can include the powering of the VAD. In light of these challenges in powering VADs and other implanted medical devices, further developments to systems, methods, and devices for wireless charging are desired.

BRIEF SUMMARY

The present application provides improved systems, methods, and devices that can improve wireless charging of an implantable medical device such as an implantable and/or implanted ventricular assist device. For example, a system can include a charging device and an implantable medical device. The charging device can include a primary coil and the implantable medical device can include a secondary coil. One or both the primary coil and the secondary coil can be deformable to, for example, allow the coil to at least partially conform with patient anatomy and improve patient comfort associated with the presence of the devices. This can include, for example, conforming with a curve of a side of a patient, a curve of the ribs of the patients, a curve of the neck of the patient, a curve of a limb, or the like.

A plurality of sensors can be coupled to the coil, and in some instances, the plurality of sensors can be connected to and/or mounted on the coil. These sensors can include one or several strain gauges, stress gauges, or the like. The plurality of sensors can be communicatingly coupled with a processor such that deformation of the coil results in one or several signals sent to the processor. The processor can use these one or several signals to determine a deformation of the coil, which deformation can be used to determine a change in the ability of the coil to send and/or receive power and/or to determine a change in the inductance of the coil. Alternatively, the processor can use these one or several signals to determine a change in the ability of the coil to send and/or receive power and/or to determine a change in the inductance of the coil.

With information relating to the change in the ability of the coil to send and/or receive power and/or relating to the change in the inductance of the coil, the processor can, in some instances, affect the driving of the coil, and specifically tune the driving of the coil to match and/or more closely match a resonant frequency of the coil. These features can, in some embodiments, improve patient comfort with the flexible coil design. Further, accounting for the change in properties of the coil allows for re-tuning of circuit based on this feedback for improved power transfer efficiency and/or to reduce heat generation in the various components for patient safety and/or comfort.

One aspect of the present disclosure relates to a ventricular assist system. The system includes: an implantable ventricular assist device including an energy storage component and a secondary coil electrically coupled to the energy storage component. The system can include an external charging device for transcutaneous charging of the ventricular assist device. The external charging device can include: a flexible housing defining an internal volume; a resonant circuit including a deformable primary coil disposed within the internal volume of the housing; a plurality of sensors coupled to the primary coil; and a processor operably coupled with the plurality of sensors. In some embodiments, the processor can determine a deformation of the primary coil based on at least one signal received from at least one of the plurality of sensors.

In some embodiments, the charging device further includes a memory containing data that link deformation of the primary coil to at least one signal received from at least one of the plurality of sensors. In some embodiments, the charging device further includes a memory containing data that link a change in impedance of the primary coil to at least one signal received from at least one of the plurality of sensors. In some embodiments, the data is stored in a lookup table.

In some embodiments, the primary coil includes a plurality of wire windings within an enclosure. In some embodiments, the enclosure is flexible, and in some embodiments, the enclosure can be made of at least one of: polyurethane; natural rubber; synthetic rubber; thermoplastic elastomer; nylon; aramid; polyvinylchloride; polyester; polymer; or the like. In some embodiments, the enclosed can be molded, extruded, layered, and/or woven. In some embodiments, the system can include a retention feature that can hold the charging device at a predetermined position of a body of a patient. In some embodiments, the primary coil is sufficiently deformable such that the impedance of the primary coil changes when the charging device is held at a position of the body of the patient by the retention feature.

In some embodiments, the plurality of sensors include at least one of: a stress gauge; or a strain gauge. In some embodiments, the charging device further includes at least one motion constraint that directs deformation of the primary coil in at least one desired direction. In some embodiments, the at least one motion constraint can limit deformation to less than a 90° bend of the primary coil. In some embodiments, the processor can trigger an alarm, which alarm can be audible, visual, and/or haptic, when at least one of: deformation of the primary coil exceeds a deformation-threshold level, or power transfer drops below a transfer-threshold level. In some embodiments, the transfer-threshold level specifies a predetermined amount of transferred power in a predetermined amount of time.

One aspect of the present disclosure relates to an inductive coupling device for transcutaneously charging a ventricular assist device implanted within a patient. The inductive coupling device includes: a resonant circuit including a coil, which coil is deformable; a plurality of sensors coupled to the coil; and a processor operably coupled to the plurality of sensors. In some embodiments, the processor can determine a deformation of the coil based on at least one signal received from at least one of the plurality of sensors.

In some embodiments, the coil includes at least one of: a primary coil; or a secondary coil. In some embodiments, the coil includes a plurality of wire windings within an enclosure. In some embodiments, the enclosure is flexible. In some embodiments, the enclosure can be made of at least one of: polyurethane; natural rubber; synthetic rubber; thermoplastic elastomer; nylon; aramid; polyvinylchloride; polyester; polymer; or the like. In some embodiments, the enclosed can be molded, extruded, layered, and/or woven.

In some embodiments, the inductive coupling device includes a housing, and in some embodiments, the housing is flexible. In some embodiments, the plurality of sensors include at least one of: a stress gauge; or a strain gauge. In some embodiments, the inductive coupling device includes at least one motion constraint that can direct deformation of the coil in at least one desired direction. In some embodiments, the at least one motion constraint can limit deformation to less than a 90° bend of the coil.

In some embodiments, the inductive coupling device includes a memory containing data that link deformation of the coil to at least one signal received from at least one of the plurality of sensors. In some embodiments, the inductive coupling device includes a memory containing data that link a change in impedance of the primary coil to at least one signal received from at least one of the plurality of sensors. In some embodiments, the data is stored in a lookup table. In some embodiments, the processor can trigger an alert and/or alarm when at least one of: deformation of the primary coil exceeds a deformation-threshold level; or power transfer drops below a transfer-threshold level. In some embodiments, the alarm can be audible, visual, and/or haptic.

One aspect of the present disclosure relates to a method of powering an implantable ventricular assist device including a secondary coil with an external charging device having a resonant circuit. The method includes: receiving a signal indicative of a change in a property of a deformable coil of the resonant circuit; determining a performance property of the coil based on the received signal; identifying an adjustment to the tuning of the resonant circuit including the coil based on the determined performance property of the coil; tuning the resonant circuit according to the adjustment to the tuning of the resonant circuit; and driving the resonant circuit.

In some embodiments, the coil includes a plurality of wire windings within an enclosure. In some embodiments, the enclosure is flexible. In some embodiments, the signal is received from at least one sensor coupled to the coil. In some embodiments, receiving the signal includes generating a signal value, and the performance property is determined based on the signal value. In some embodiments, determining the performance property based on the signal value includes: querying a memory with the signal value; and receiving one or several values indicative of the performance property from the memory.

In some embodiments, the performance property can be at least one of: a deformation of the coil; a bending of the coil; a flexing of the coil; an inductance of the coil; or a change in inductance of the coil. In some embodiments, the adjustment to the tuning of the resonant circuit is identified to maintain a resonant frequency of the resonant circuit within a target range or at a target frequency. In some embodiments, the adjustment to the tuning of the resonant circuit can include a change in a capacitance of the resonant circuit. In some embodiments, tuning the resonant circuit includes changing the capacitance of the resonant circuit.

In some embodiments, the resonant circuit comprises a variable-capacitance capacitor. In some embodiments, the adjustment to the tuning of the resonant circuit comprise a change in the capacitance of the variable-capacitance capacitor. In some embodiments, tuning the resonant circuit comprises changing the capacitance of the variable-capacitance capacitor.

In some embodiments, the method includes determining the acceptability of the performance property of the coil. In some embodiments, the method includes triggering an alarm the performance property is unacceptable. In some embodiments, the performance property is unacceptable when at least one of: deformation of the primary coil exceeds a deformation-threshold level; or power transfer drops below a transfer-threshold level. In some embodiments, the transfer-threshold level specifies a predetermined amount of transferred power in a predetermined amount of time. In some embodiments, the alarm is at least one of: audible; visual; or haptic.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

Figure 1:
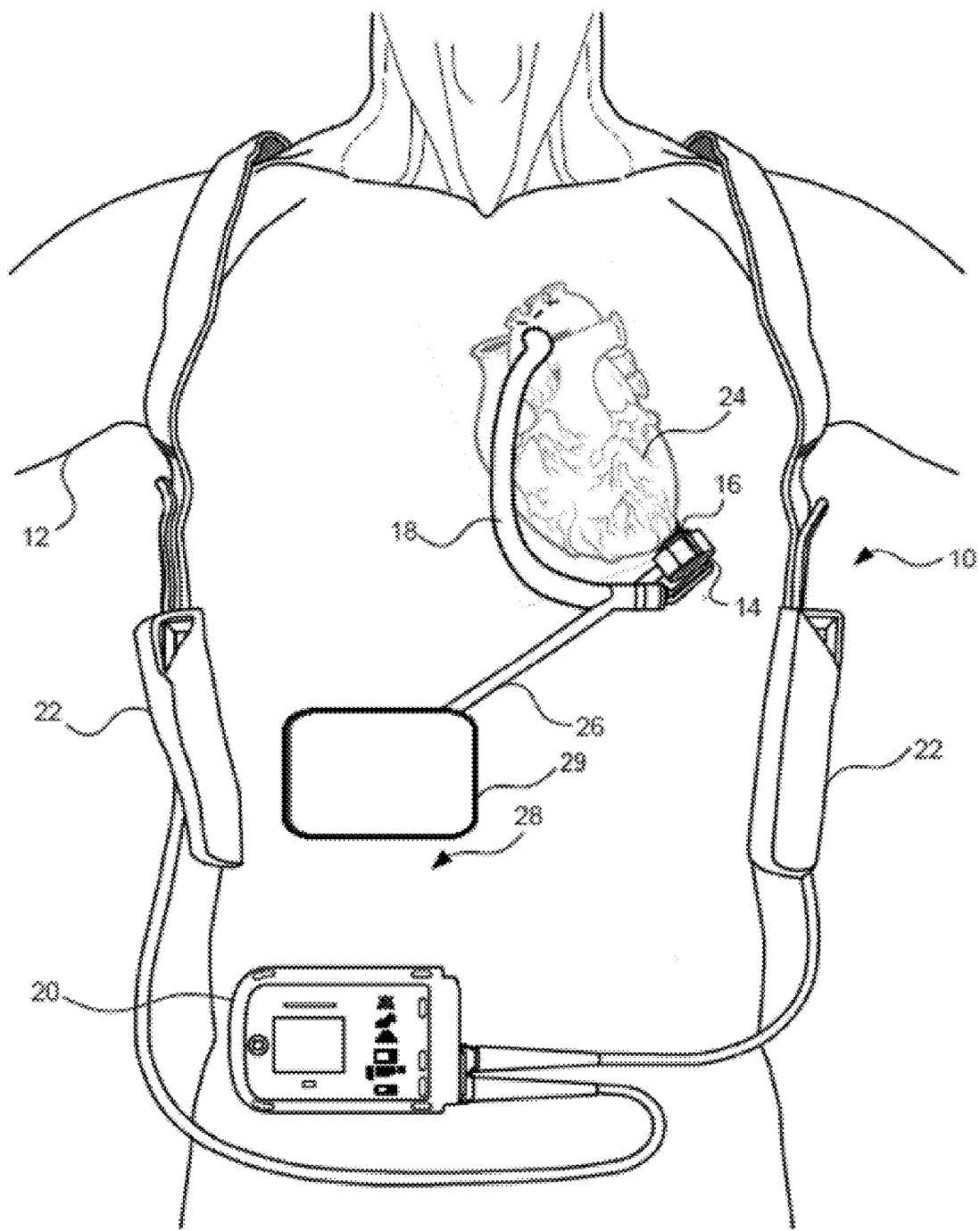
FIG. 1 is an illustration of a mechanical circulatory support system implanted in a patient's body.

In implantable medical devices that utilize electrical power to enable their operation, power can provided through the use of a cord that extends through the skin to physically connect the implantable medical device to an external power source or alternatively through the use of features that allow wireless charging of the implantable medical device.

These problems from external powering of the implantable medical devices are particularly apparent in medical devices consuming relatively large amounts of power. For example, an implantable blood pump such as a VAD may use significantly more power than, for example, a pacemaker. Such implantable medical devices that consume large amounts of power can be constantly charged by an external charger that may be held proximate to a portion of a patient's body and/or be charged for significant periods of time by the external charger being held proximate to the portion of the patient's body. This continuous or extended use of the external charger can cause discomfort.

In addition to this, implantable medical devices may be implanted in non-static portions of the patient's body. This can include, for example, placement of the implantable medical device close to a rib, within portions of the abdomen subject to bending, or near a joint. In such positions, the rigidity of the implantable medical device can create discomfort.

These problems can be addressed via use of flexible and/or deformable coil which can be, for example, a primary coil of the charging device and/or a secondary coil of the implantable medical device. This deformable can be temporarily and/or permanently elastically deformable so as to conform and/or partially conform with one or more structure of the patient's body such as, for example, the skin of the patient's body, a bone such as one or several ribs of the patient's body, one or several muscles of the patient's body, or the like. The coil can be, in some embodiments, contained within a deformable and/or flexible housing that can flex and/or deform to the same extent as the coil. This deformation of the coils can, in some embodiments, change an impedance of the coil, which can affect a resonant frequency of a resonant circuit of which the coil is a part. This change to the resonant frequency can result in inefficient coupling with another device and in the inefficient transfer of energy from one device to another as the resonant frequencies of resonant circuits in both devices may be insufficiently similar to allow efficient coupling.

A plurality of sensors can be coupled to the coil, and in some embodiments, these sensors can be attached to the coil. These sensors can detect a change in the shape of the coil via, for example, a detection of a stress, a strain, or the like. When the coils are deformed, flexed, and/or bent, some or all of the plurality of sensors can generate one or several signals which can be received by a processor. The processor can, based on the received one or several signals, determine deformation, flexing, and/or bending of the coil and/or determine a change of an electrical property of the coil such as, for example, a change in the inductance of the coil. Based on this changed electrical property of the coil, the processor can determine an adjustment to the tuning of the resonant circuit including the coil, which adjustment to the resonant circuit can improve energy transfer efficiency.

FIG. 1 is an illustration of a mechanical circulatory support system 10 implanted in a patient's body 12. The mechanical circulatory support system 10 comprises a implantable blood pump 14, ventricular cuff 16, outflow cannula 18, system controller 20, and external power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 through 4, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during external power source 22 powered operation. A driveline 26 couples the implanted blood pump 14 to an internal module 29 can be located within the patient's body, and specifically can be located within the patient's abdomen 28. The internal module 29 can wirelessly connect the implanted blood pump 14 to power source 22 and/or to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. In some embodiments, the system can include one, two, or more external power sources 22. It will be appreciated that although the system controller 20 is illustrated outside/external to the patient body, system controller 20 may be partially or fully implantable within the patient, as separate components or integrated with the blood bump 14. Examples of such modifications are further described in U.S. Pat. No. 8,562,508 and U.S. Patent Publication No. 2013/0127253, all of which are incorporated herein by reference for all purposes in their entirety.

Figure 2:
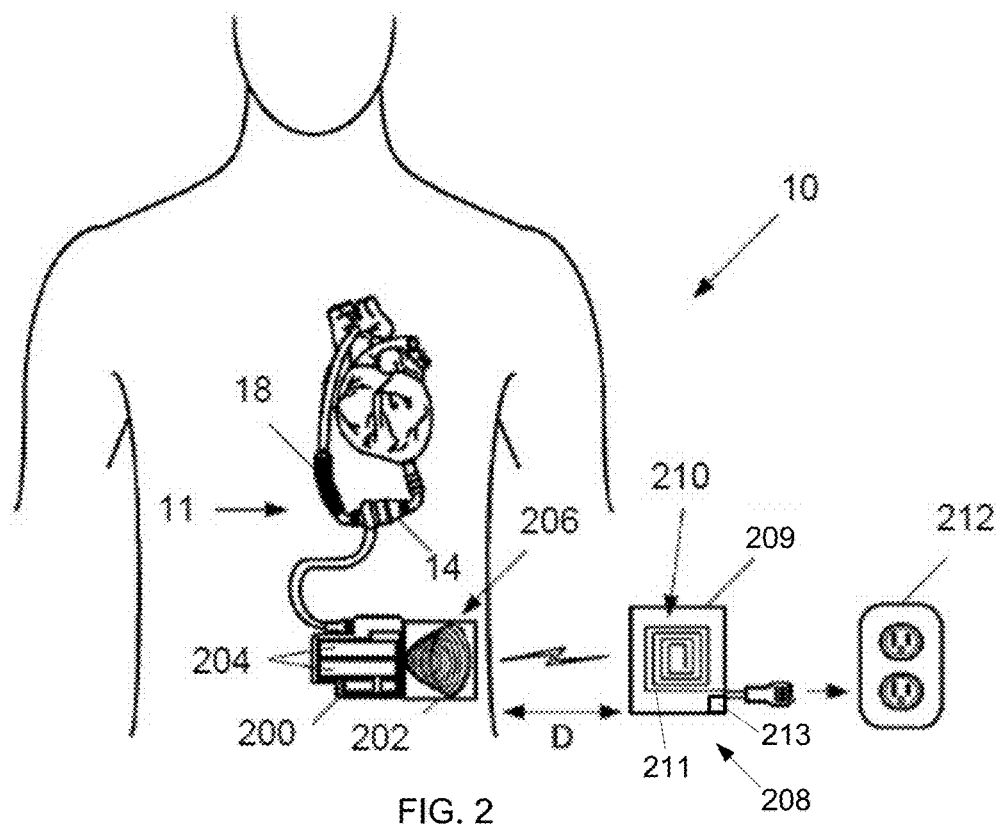
FIG. 2 is an illustration of one embodiment of a mechanical circulatory support system with a Transcutaneous Energy Transfer System (TETS) implanted in a patient's body in a first position.
Figure 3:
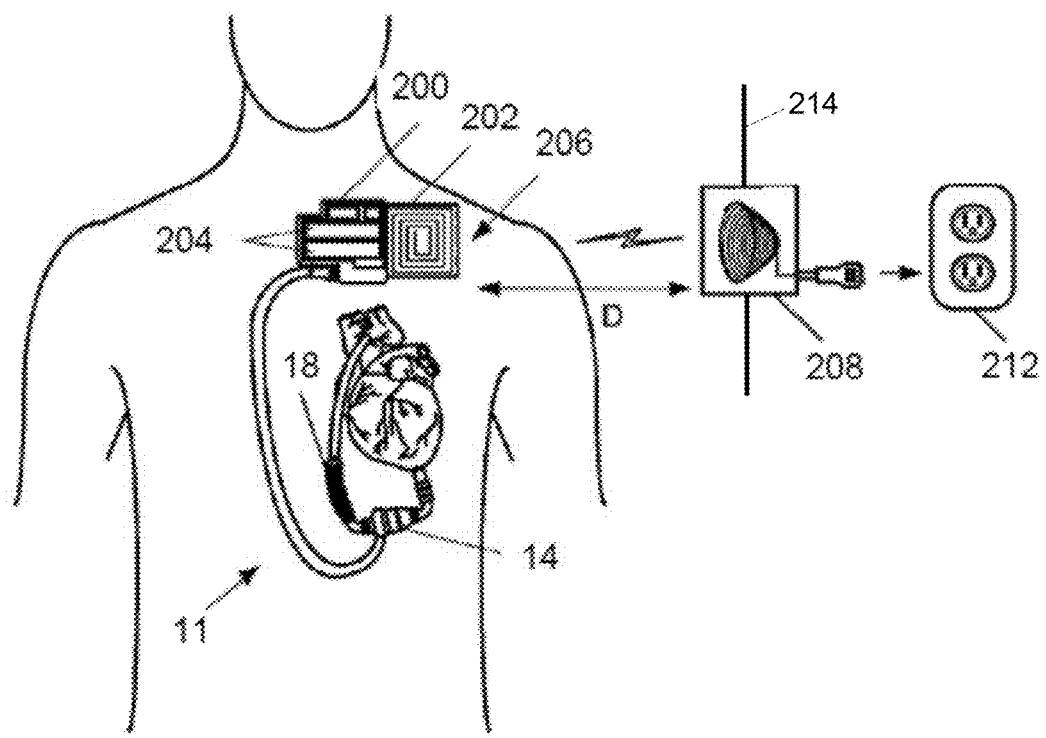
FIG. 3 is an illustration of one embodiment of a mechanical circulatory support system with a Transcutaneous Energy Transfer System (TETS) implanted in a patient's body in a second position.
Figure 4:
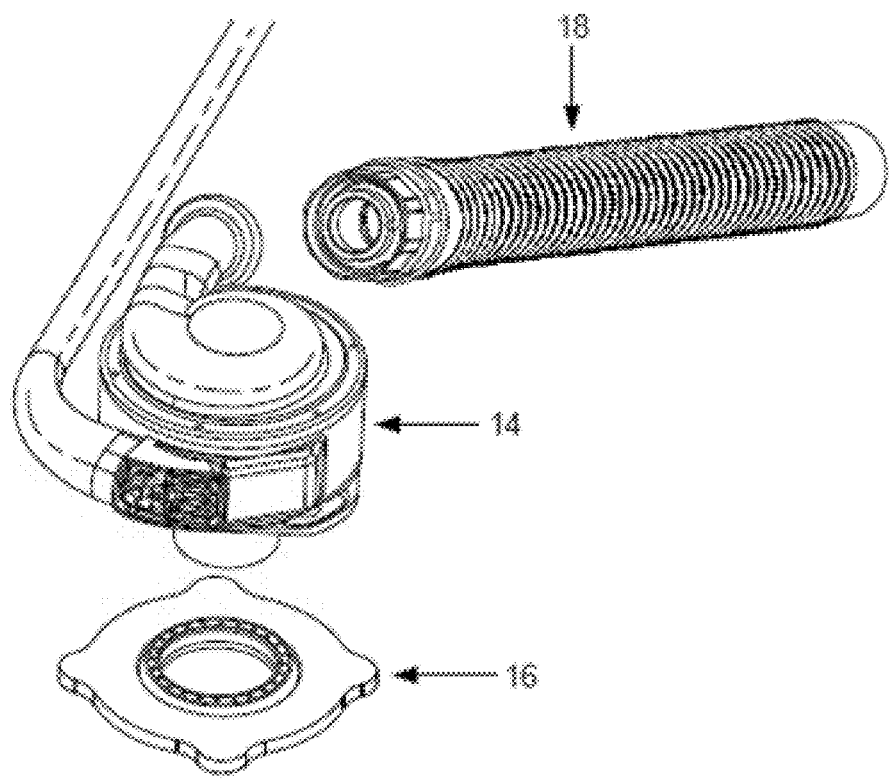
FIG. 4 is an exploded view of certain components of the circulatory support system that are implanted in a patient's body.

FIGS. 2 and 3 illustrates exemplary embodiments of the mechanical circulatory support system 10 with internal components 11 according to embodiments of the present invention. The internal components 11 include a cannula 18, a blood pump 14, a rechargeable power storage device 200, also referred to herein as an implantable power supply 200, and a power receiver unit 202. The rechargeable power storage device 200 may include two or more energy storage components 204, which can be, for example, batteries including rechargeable batteries, capacitors, fuel cells, or the like. In some embodiments, these energy storage components 204 can include a first energy storage component and a second energy storage component. In some embodiments, the first and second energy storage components can be matched, and in other embodiments, the first and second energy storage components can be unmatched. In some embodiments, for example, the first and second energy storage components can have the same voltages and/or the same number of cells, and in some embodiments, the first and second energy storage components can have different voltages and/or different numbers of cells.

The rechargeable power storage device 200 can be a part of the blood pump 14, or can be separate from the blood pump 14. In some embodiments, the rechargeable power storage device 200 can be implanted in a location away from the cannula 18, for example, in the lower abdominal as shown in FIG. 2. The power receiving unit 202 includes a TETS receiver 206 that can be, for example, a receiver, a resonator, and inductive coil or the like, that can be coupled to the power storage device 200, which is the electrical load of the power receiver unit 202. In the embodiment as shown in FIG. 2, because the power receiver unit 202 is implanted in the lower abdominal area where there may be less spatial constraints on the size and shape of the TETS receiver 206, the TETS receiver 206 can be a non-planar resonator and can span a non-degenerate two-dimensional surface including any of the surfaces described above. In some embodiments, the resonant frequency of the TETS receiver 206 can be in a range of 100 kHz to 10 MHz. In an exemplary embodiment, the resonant frequency of the receiver resonator 206 can be 100 kHz, 500 kHz, 1 MHz, or 10 MHz. In other embodiments, another resonant frequency that is safe for the human body can be used.

The mechanical circulatory support system 10 also includes a power transmitter unit 208, also referred to herein as a non-implantable charger 208 and/or as a charging device 208, that is external to the patient. The transmitter unit 208 can comprise a housing 209 that can define an internal volume and that can be a deformable and/or flexible housing 209 that can include a transmitter resonator 210, also referred to herein as a TETS transmitter 210. The transmitter resonator 210 can include, for example, a coil 211, including an inductive coil that is flexible, deformable, and/or flexible. In some embodiments, the coil 211 can be configured to deform to at least partially conform with patient anatomy.

In some embodiments, the housing 209 can be more flexible than the coil 211, less flexible than the coil 211, or equally flexible with the coil 211. In some embodiments, for example, when the coil 211 and/or housing 209 including the coil 211 are placed on the patient's body as part of the recharging, the coil 211 and/or the housing 209 elastically deform to conform to at least a portion of the patient's body. This deformation can occur with a load of less than 1 pound, less than 2 pounds, less than 5 pounds, less than 10 pounds, less than 20 pounds, or any other or intermediate load. In some embodiments, the deformation, bending, and/or flexing of the coil can be limited by at least one motion constraint 213. The motion constraint 213 can be a part of the housing 209, coupled to the coil 211, and/or coupled to the housing 209. In some embodiments, the motion constraint 213 can direct deformation in at least one desired direction, can limit directions in which the coil 211 and/or housing 209 can bend, flex, and/or deform, and/or can limit the extent to which the coil 211 and/or the housing 209 can bend, flex, and/or deform. In some embodiments, for example, the motion constraint 213 can prevent the coil 211 and/or housing 209 from bending more than 25°, more than 35°, more than 45°, more than 55°, more than 75°, more than 90°, more than 120°, more than 150°, more than a value between 45° and 100°, and/or more than any other or intermediate value.

In some embodiments, the power transmitted unit 208 can be configured to be coupled to an electric power source 212 such as an electrical wall outlet or external power sources 22. When the transmitter unit 208 is powered by, for example, connection to the electric power source 212, an electrical current is generated in the coil of the transmitter resonator 210. The resonant frequency of the transmitter resonator 210 can be in a range of 100 kHz to 10 MHz, or in a range of 100 kHz to 20 MHz. In an exemplary embodiment, the resonant frequency of the transmitter resonator 210 can be approximately: 100 kHz, 500 kHz, 1 MHz, 10 MHz, 15 MHz, or 20 MHz. In other embodiments, another resonant frequency that is safe for the human body can be used.

The transmitter resonator 210 as part of the transmitter unit 208 may be embedded in a stationary object such as a wall, a chair, a bed, or other fixtures such as a car seat or objects that do not move by themselves without external control or human assistance. The source of power for a stationary and embedded transmitter resonator is generally alternating current from an electric outlet, but can also be direct current from a battery source. In some embodiments, the transmitter unit 208 may include one or several retention features 214 that can be configured to hold the charging device 208 at a position relative to a portion of a patient's body. In some embodiments, for example, the retention feature 214 can be sufficiently strong and/or the coil 211 and/or the housing 209 can be sufficiently deformable such that the charging coil 211 and/or the housing 209 deforms when held at a position relative to the portion of the patient's body by the retention features 214 and/or such that the impedance of the coil 211 changes when the charging device 208 is held at a position of the body of the patient by the retention feature 214. In some embodiments, the transmitter resonator 210 may be part of a piece of wearable clothing such as a vest or a jacket, or other wearable accessories. In the case of a transmitter resonator that is embedded into a piece of clothing or object wearable by a person that moves with a person, the source of power would be portable sized rechargeable batteries that also could be worn by the patient.

When the receiver unit 202 in the patient comes within a separation distance D of the transmitter unit 208, the mechanical circulatory support system 10 is able to wirelessly transfer energy from the transmitter unit 208 to the receiver unit 202 to recharge the power storage device 200 of the internal components 11. In one embodiment, at a given separation distance D being in the range of 2.5 cm to 35 cm, the transmitter unit 208 is able to deliver power in the range of 5 W to 20 W to the receiver unit 202 to recharge the batteries 204 in the power storage device 200 of the internal components 11.

Figure 5:
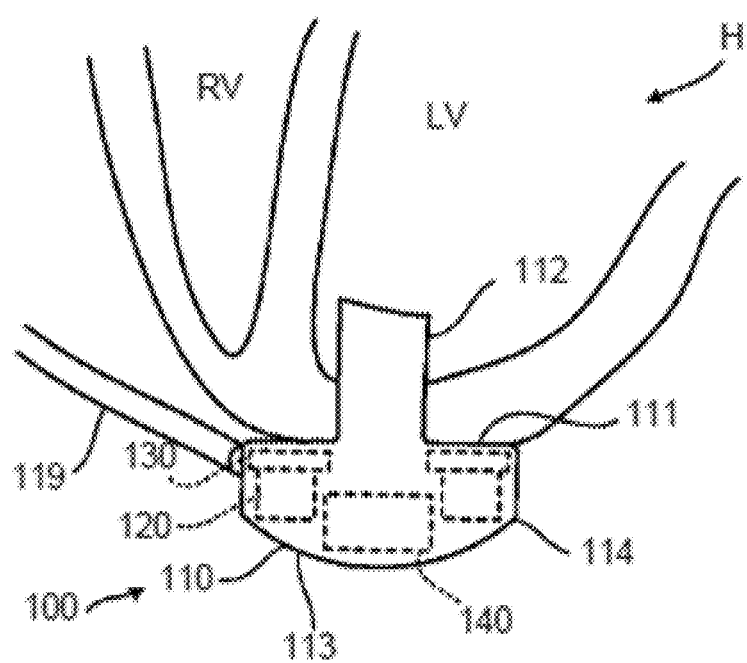
FIG. 5 is an illustration of a blood pump in an operational position implanted in a patient's body.
Figure 6:
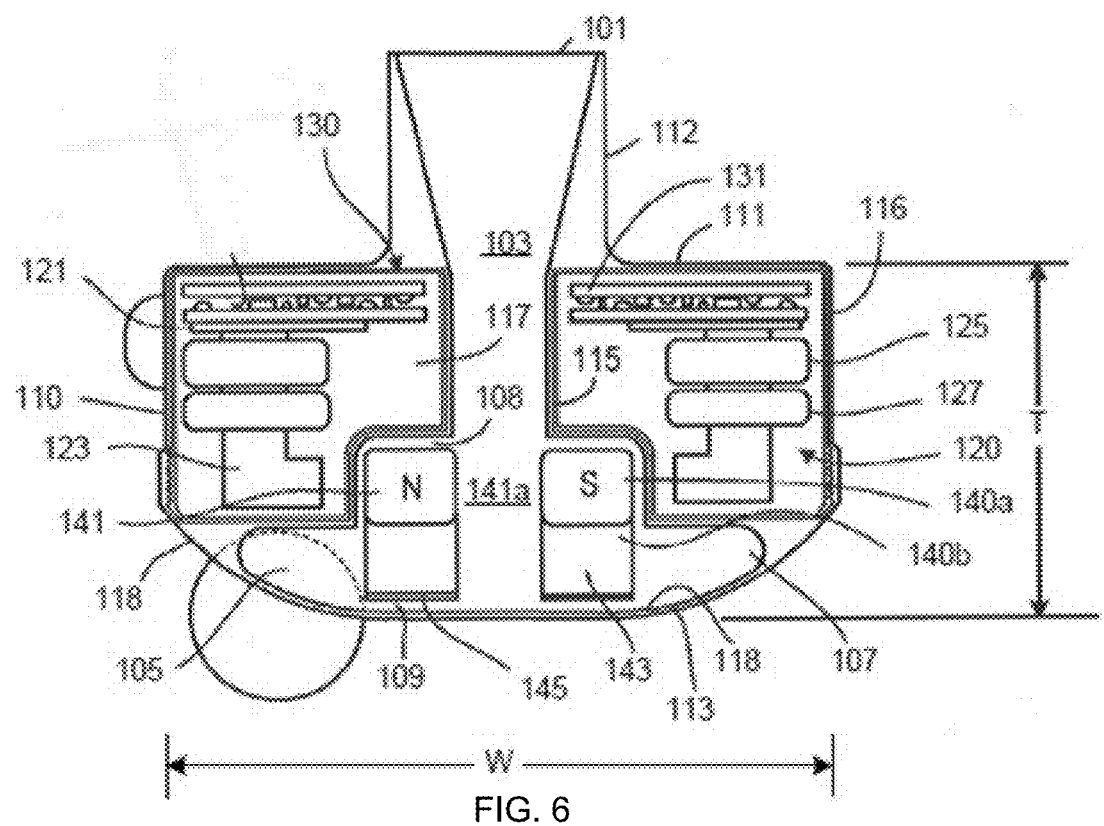
FIG. 6 is a cross-sectional view of the blood pump of FIG. 5.
Figure 7:
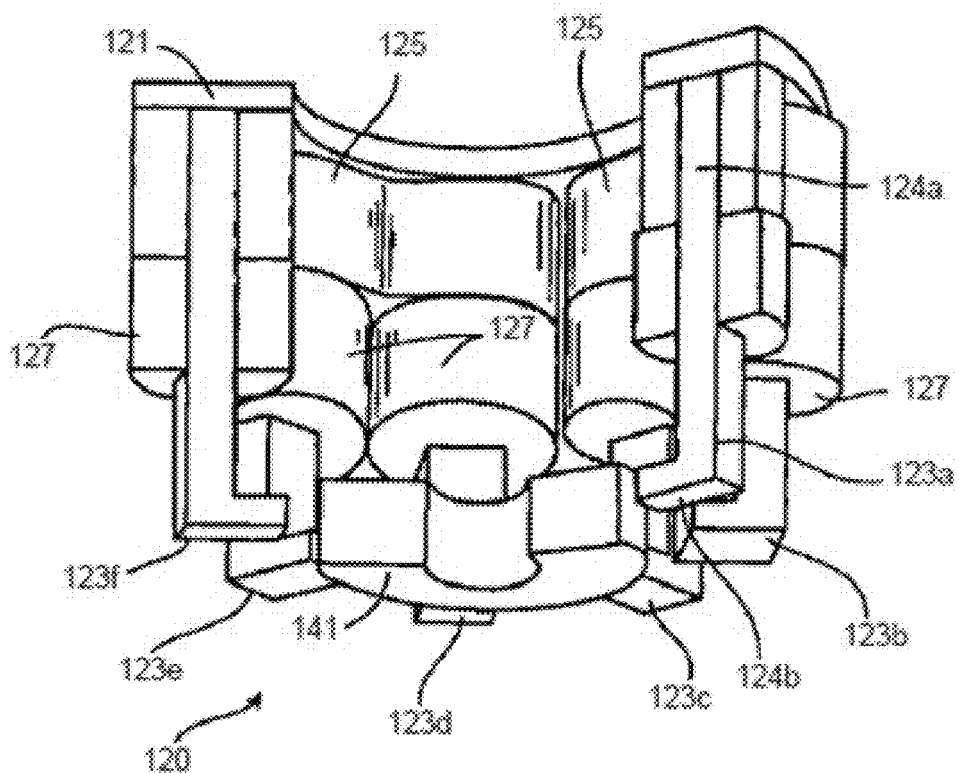
FIG. 7 is a partial cut-away perspective view of a stator of a blood pump.

With reference to FIGS. 5 to 7, a left ventricular assist blood pump 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 4 to 6, for example.

Referring to FIG. 6, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 6 and 7, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply such as the internal module 29 via a cable 119 (FIG. 5). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 8:
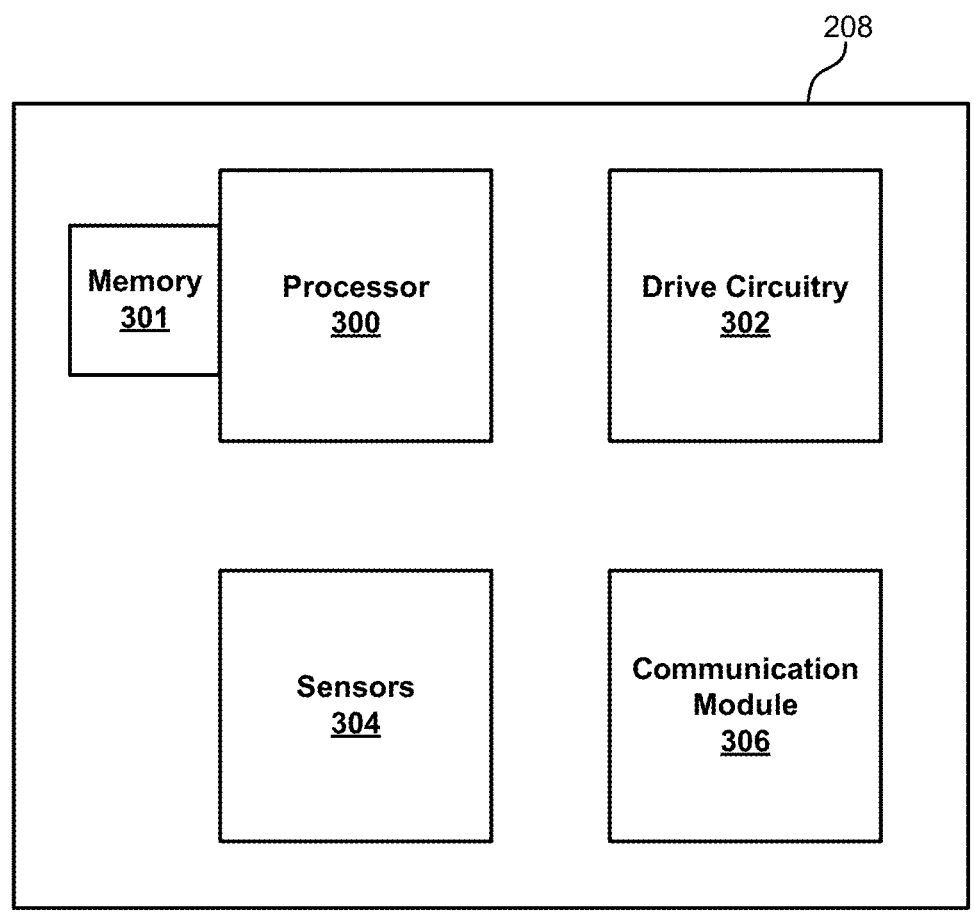
FIG. 8 is a schematic illustration of one embodiment of the transmitter unit.

FIG. 8 is a schematic illustration of one embodiment of the transmitter unit 208. In some embodiments, the transmitter unit 208 can be a part of the controller 20, and in some embodiments, the transmitter unit 208 can be independent of the controller 20. The transmitter unit 208 can be configured to transmit power to the implanted blood pump 14 via, for example, the internal module 29. The transmitter unit 208 can include a processor 300, drive circuitry 302, a plurality of sensors 304, and/or a communications module 306, some or all of which can be, in some embodiments, contained within the internal volume defined by the housing 209 of the transmitter unit 208. The processor 300 which can be associated with memory 301 which can comprise one or several stored instructions executable by the processor 300 can be adapted to provide instructions to and receive information from the other components of the mechanical circulatory support system 10. The processor 300 can include a microprocessor, such as a commercially available microprocessor from Intel® or Advanced Micro Devices, Inc.®, or the like.

The drive circuitry 302 can comprise circuitry for transmitting energy from the transmitter unit 208 to the internal module 29. This can include a resonant circuit that can be, any circuit configured to wireless energy transfer including, for example, at least one LC or RLC circuit. In some embodiments, the drive circuitry 302 can further comprise a driver configured to provide energy to the resonant circuit. In some embodiments, the driver can provide energy to the resonant circuit at a frequency corresponding to the resonant frequency of the resonant circuit. In some embodiments, the drive circuitry can comprise a coil that can be, for example, a primary coil.

In some embodiments, the drive circuitry 302 can be configured to compensate for changes in inductance of the coil. This can include, for example, changing an attribute of the resonant circuit to maintain a desired resonant frequency when the inductance of the coil changes. In some embodiments, for example, the capacitor within the resonant circuit can comprise a variable capacitor that can be adjusted to maintain the resonant frequency of the resonant circuit at a target frequency and/or within a target range if the inductance of the coil changes.

In some embodiments, the transmitter unit 208 can comprise the plurality of sensors 304. The plurality of sensors can be coupled to the coil and can be configured to generate one or several signals indicative of a change in an attribute of the coil. This attribute can include, for example, a change in a shape of the coil, a change in the size of the coil such as, for example, a change in a diameter of the coil, and/or a change in an electrical property of the coil such as, for example, a change in the inductance of the coil. At least one of the plurality of sensors can comprise, for example, one or several stress gauges, one or several strain gauges, one or several electrical attribute sensors, or the like. In some embodiments, some or all of the plurality of sensors can comprise one or several optical sensors such as, for example, one or several optical strain gauges.

In some embodiments, some or all of the plurality of sensors can be communicatingly coupled to the processor 300. In some embodiments, these signals can be indicative of a stress or strain in the coil, which stress or strain can be indicative of a bending, flexing, and/or deforming of the coil. The processor 300 can be configured to receive one or several signals from one or several of the plurality of sensors 304 and determine an attribute of the coil based on those received one or several signals. This attribute can comprise, for example, a deformation, an inductance, a change in inductance, or the like. In some embodiments, for example, the processor 300 can determine this attribute based on information stored in the memory 301. In some embodiments, for example, the memory can comprise data linking signal values with deformations of the coil and/or with an impedance or change of impedance of the coil. In some embodiments, for example, this data can be used to identify a change in a performance property of the resonant circuit and/or of the coil based on the received signal values. In one embodiment, for example, a signal can be received, which signal characterizes an attribute of the coil, and a value for the signal can be determined. A database containing the data linking changes in performance properties of the coil to signals from the at least one sensor can be queries with the value of the received signal and, in response to the query, one or several performance properties of the coil and/or one or several values indicative of performance properties can be returned. This data can be stored in a database, as a curve fit, and/or in a lookup table.

The communication module can be configured to communicate with one or several components and/or devices that are not a part of the transmitter unit 208. This can include, for example, wireless communication with the receiver unit 29, wireless communication with the blood pump 14, wired communication with one or several power sources 22, or the like. In some embodiments, the communications module 306 can comprise an antenna, a transceiver, a transmitter, a receiver, or the like. The communications module 306 can be communicatingly coupled with the processor 300.

Figure 9:
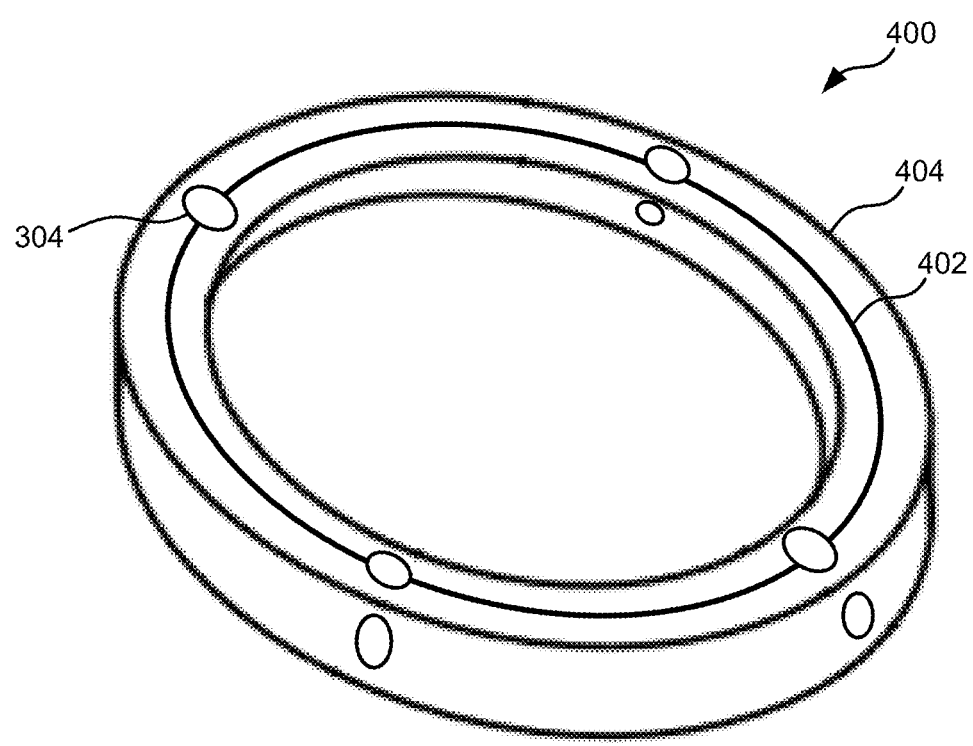
FIG. 9 is a perspective view of one embodiment of a coil.

FIG. 9 is a perspective view of one embodiment of a coil 400 of the drive circuitry 302. Although the coil 400 of FIG. 9 is identified as part of the transmitter unit 208, and thus is the primary coil, in some embodiments, the coil 400 can be part of the power receiver unit 202, and thus is a secondary coil. The coil can comprise a plurality of wire windings 402 that can be encased within an enclosure 404. The wire windings 402 can be deformable, flexible, and/or bendable. The wire windings 402 can comprise any desired number of loops of any desired wire. In some embodiments, for example, the wire windings 402 can comprise at least 5 loops of wire, at least 10 loops of wire, at least 20 loops of wire, at least 30 loops of wire, at least 40 loops of wire, at least 50 loops of wire, at least 75 loops of wire, at least 100 loops of wire, at least 150 loops of wire, at least 200 loops of wire, at least 500 loops of wire, at least 1,000 loops of wire, between 10 and 2,000 loops of wire, or any other or intermediate number of loops of wire.

The enclosure 404 can comprise a flexible, bendable, and/or deformable enclosure 404. The enclosure can enclose the wire windings 402 to protect the wire windings 402. In some embodiments, the enclosure 404 can be can be more flexible than the coil 211 and/or with the wire winding 402, less flexible than the coil 211 and/or with the wire winding 402, or equally flexible with the coil 211 and/or with the wire winding 402. In some embodiments, the coil 400, and thus the enclosure 404 and the wire windings 402, can flex, bend, and/or deform in a single plane and/or with a single bending radius, or in multiple planes and/or with multiple bending radii. In some embodiments, the enclosure 404 can comprise at least one of: polyurethane; natural rubber; synthetic rubber; thermoplastic elastomer; nylon; aramid; polyvinylchloride; polyester; polymer; or the like. In some embodiments, the enclosed can be molded, extruded, layered, and/or woven.

The coil 400 can be coupled to the plurality of sensors 304. The sensors 304 can be, in some embodiments, attached to the coil 400, and in some embodiments, the sensors 304 can be coupled to the coil 400 via one or several: mechanical actuators; fulcrums; levers; cogs; or the like. The sensors 304 can, in some embodiments, be pairwise positioned on the coil 400 such that each pair monitors bending for one degree of freedom of the coil 400. These sensors 304 can comprises, for example, one or several strain gauges, linear or angular displacement gauges, stress gauges, pressure gauges, or the like.

Figure 10:
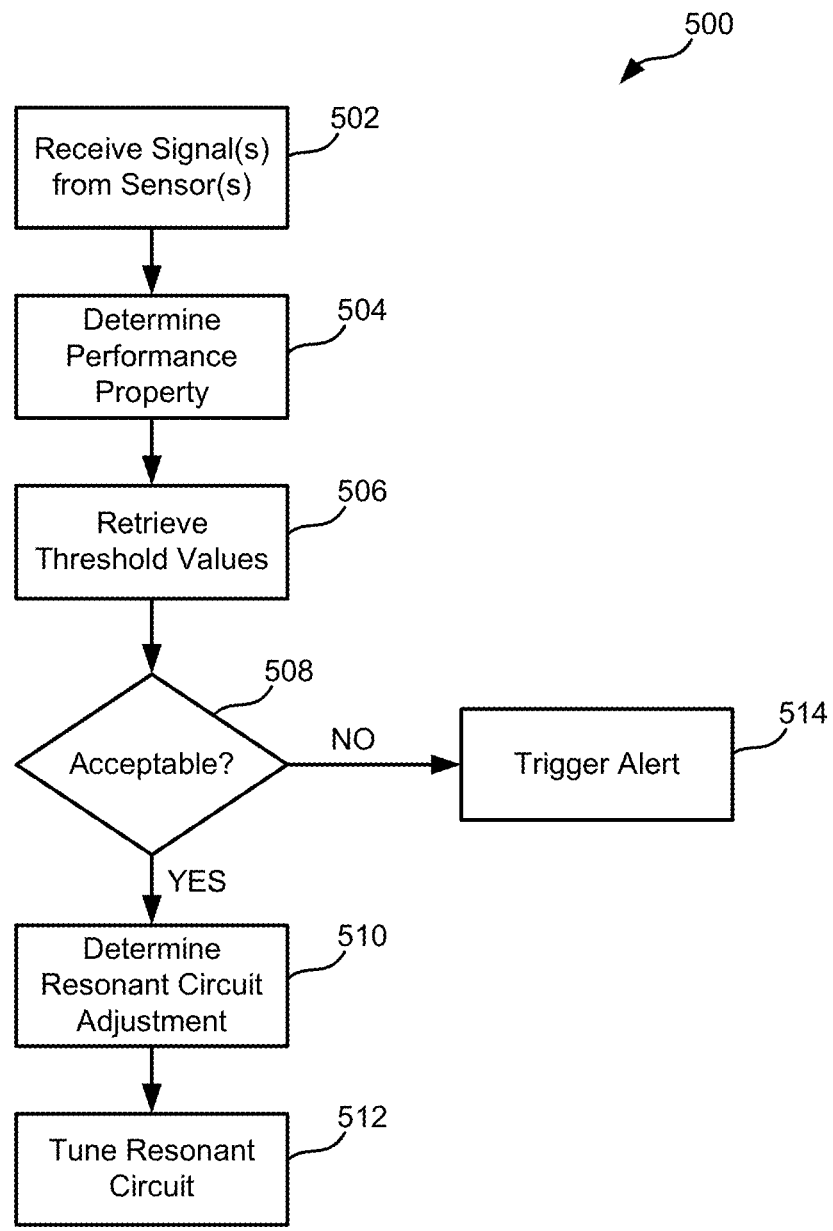
FIG. 10 is a flowchart illustrating one embodiment of a process for operation of the charging device.

FIG. 10 is a flowchart illustrating one embodiment of a process 500 for operation of all or portions of the mechanical circulatory support system 10, and specifically for operation of all or portions of the charging device 208. In some embodiments, the process 500 can be performed to control the tuning of the resonant circuit of the drive circuitry 302 of the charging device 208. The process 500 begins at block 502, wherein at least one signal is received from at least one sensor 304 coupled to the coil 400 of the resonant circuit. In some embodiments, the at least one can be generated by the at least one sensor 304 in response to a change of a property of the coil 400 subsequent to a deformation, bending, and/or flexing of the coil. The at least one signal can be received by the processor 300 of the charging device. In some embodiments, the signal of block 502 can be received subsequent deformation and/or bending of the coil and/or subsequent to positioning of the coil on or adjacent to a portion of a patient's anatomy causing a deformation and/or bending of the coil. In some embodiments, an subsequent to receipt of the ate least one signal, at least one signal value can be generated from the at least one signal, which signal value characterizes the received signal.

After the signal has been received, the process 500 proceeds to block 504, wherein a performance property is determined. In some embodiments, the performance property can characterize an attribute of the coil such as, for example, the inductance of the coil 400, a change in the inductance of the coil 400, a deformation, bending, and/or flexing of the coil 400, or the like. In some embodiments, the performance property can characterize a charging rate and/or a power transmission rate. In some embodiments, the performance property can characterize a power transmission rate over a predetermined period of time. The performance property can be determined by the processor 300 based on the signal received in block 502 and/or based on other information received from the receiver unit 202. In some embodiments, the determining of the performance property can comprise querying memory with the signal, and specifically with the signal value. In some embodiments, and as a response to the query, one or several values characterizing the performance property can be returned.

After the performance property has been determined, the process 500 proceeds to block 506, wherein one or several threshold values are retrieved by the processor 300 from the memory 301. In some embodiments, these threshold values can delineate between acceptable and unacceptable performance properties. In some embodiments, for example, a threshold value can delineate between acceptable deformation, bending, and/or flexing and unacceptable bending, deformation, and/or flexing. In some embodiments, the threshold value can delineate between acceptable charging rates and/or power transmission rates and unacceptable charging rates and/or power transmission rates.

After the threshold values have been retrieved, the process 500 proceeds to decision state 508, wherein it is determined if the determined performance property is acceptable. In some embodiments, this can include determining whether the received signals indicate bending, flexing, and/or deformation that is acceptable or unacceptable and/or determining whether the charging rates and/or power transmission rates are acceptable or unacceptable. This determination can be made by the processor 300.

If it is determined that the performance property is acceptable, then the process 500 proceeds to block 510, wherein an adjustment to the resonant circuit is determined. In some embodiments, this can include determine a change in an attribute of the resonant circuit to maintain a desired resonant frequency based on the determined deformation of the coil 400, the changed inductance of the coil 400, and/or change in the inductance of the coil 400. In some embodiments, for example, this can include determining a change in the capacitance of the resonant circuit, and specifically a change in the capacitance of the variable capacitor within the resonant circuit. This determined adjustment to the resonant circuit can maintain the resonant frequency of the resonant circuit at the target frequency and/or within the target range if the inductance of the coil changes. This adjustment can determined by the processor 300, In some embodiments, this adjustment can be determined by the processor 300 based on the received signals and information in the memory 301 linking signal values to changes in properties of the coil, which properties can include, for example, shape, inductance, deformation, or the like.

After the adjustment to the resonant circuit has been determined, the process 500 proceeds to block 512, wherein the resonant circuit is tuned. In some embodiments, the tuning of the resonant circuit can comprise the generation and sending of one or several control signals by the processor to components of the drive circuitry 302. In some embodiments, these control signals can direct the variable capacitor to change its capacitance. In some embodiments, in which the coil comprises the primary coil, and as a part of the tuning of the resonant circuit and/or subsequent to the tuning of the resonant circuit, the drive circuitry 302 can drive the resonant circuit to wirelessly transfer power from a primary coil to the secondary coil.

Returning again to decision state 508, if it is determined that the performance properties are unacceptable, then the process 500 proceeds to block 514, wherein an alert is triggered. In some embodiments, the triggering of the alert can include the generation of an audible, visual, and/or tactile indicator of the alert status, which indicator can serve to make the patient aware of the unacceptable performance property. In some embodiments, the triggering of the alert can include the generation and sending of a message to one or several devices communicatingly coupled with the mechanical circulatory support system 10 such as, for example, one or several patient devices, one or several doctor devices, or the like. These message can, in some embodiments, include a time stamp associated with the alert, identify the performance property giving rise the alert, identify the patient associated with the alert, identify one or several remedial steps, or the like.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A ventricular assist system comprising:
   an implantable ventricular assist device;
   an implantable energy storage component for storing energy for powering the ventricular assist device;
   an implantable secondary coil electrically coupled to the energy storage component; and
   an external charging device for transcutaneous charging of the energy storage component, the external charging device comprising:
   a flexible housing defining an internal volume;
   a resonant circuit comprising a deformable primary coil disposed within the internal volume of the flexible housing;
   a plurality of sensors coupled to the primary coil; and
   a processor operably coupled with the plurality of sensors, wherein the processor is configured to determine an amount of bending of the primary coil based on at least one signal received from at least one of the plurality of sensors.

2. The system of claim 1, wherein the charging device further comprises a memory comprising data that link the determined amount of bending of the primary coil to at least one signal received from at least one of the plurality of sensors.

3. The system of claim 1, wherein the charging device further comprises a memory comprising data that link a change in impedance of the primary coil to at least one signal received from at least one of the plurality of sensors.

4. The system of claim 3, wherein the data is stored in a lookup table.

5. The system of claim 1, wherein the primary coil comprises a plurality of wire windings within an enclosure.

6. The system of claim 5, wherein the enclosure is flexible.

7. The system of claim 6, wherein the enclosure comprises at least one of: polyurethane; natural rubber; synthetic rubber; thermoplastic elastomer; nylon; aramid; polyvinylchloride; polyester; or polymer.

8. The system of claim 1, further comprising a retention feature configured to hold the charging device at a desired position of a body of a patient.

9. The system of claim 8, wherein the primary coil is sufficiently deformable such that an impedance of the primary coil changes when the charging device is held at a predetermined position of the body of the patient by the retention feature.

10. The system of claim 1, wherein the plurality of sensors comprises at least one of: a stress gauge; or a strain gauge.

11. The system of claim 1, wherein the charging device further comprises at least one motion constraint configured to limit bending of the primary coil in at least one desired direction.

12. The system of claim 11, wherein the at least one motion constraint is configured to limit bending of the primary coil to less than a 90° bend of the primary coil.

13. The system claim 1, wherein the processor is configured to trigger an alarm when at least one of bending of the primary coil exceeds a bending-threshold level; or power transfer drops below a transfer-threshold level.

14. The system of claim 13, wherein the transfer-threshold level specifies a predetermined amount of transferred power in a predetermined amount of time.

15. The system of claim 13, wherein the alarm is audible, visual, or haptic.

16. The system of claim 1, wherein a first pair of sensors of the plurality of sensors is positioned on the primary coil to monitor bending of the primary coil in a first direction.

17. The system of claim 16, wherein a second pair of sensors of the plurality of sensors is positioned on the primary coil to monitor bending of the primary coil in a second direction that is different from the first direction.

18. An inductive coupling device for transcutaneously charging a ventricular assist device implanted within a patient, the inductive coupling device comprising:
   a resonant circuit comprising a coil, wherein the coil is bendable;
   a plurality of sensors coupled to the coil; and
   a processor operably coupled to the plurality of sensors, wherein the processor is configured to determine an amount of bending of the coil based on at least one signal received from at least one of the plurality of sensors.

19. The inductive coupling device of claim 18, wherein the coil comprises at least one of: a primary coil; or a secondary coil.

20. The inductive coupling device of claim 18, wherein the coil comprises a plurality of wire windings within an enclosure.

21. The inductive coupling device of claim 20, wherein the enclosure is flexible.

22. The inductive coupling device of claim 20, wherein the enclosure comprises at least one of: polyurethane; natural rubber; synthetic rubber; thermoplastic elastomer; nylon; aramid; polyvinylchloride; polyester; or polymer.

23. The inductive coupling device of claim 18, further comprising a housing, wherein the housing is flexible.

24. The inductive coupling device of claim 18, wherein the plurality of sensors comprises at least one of: a stress gauge; or a strain gauge.

25. The inductive coupling device of claim 18, further comprising at least one motion constraint configured to limit bending of the coil in at least one desired direction.

26. The inductive coupling device of claim 25, wherein the at least one motion constraint is configured to limit bending of the coil to less than a 90° bend of the coil.

27. The inductive coupling device of claim 18, further comprising a memory comprising data that link the determined amount of bending of the coil to at least one signal received from at least one of the plurality of sensors.

28. The inductive coupling device of claim 18, further comprising a memory comprising data that link a change in impedance of the coil to at least one signal received from at least one of the plurality of sensors.

29. The inductive coupling device of claim 28, wherein the data is stored in a lookup table.

30. The inductive coupling device of claim 18, wherein the processor is configured to trigger an alarm when at least one of: bending of the coil exceeds a bending-threshold level; or power transfer drops below a transfer-threshold level.

31. The inductive couple device of claim 30, wherein the alarm is audible, visual, or haptic.

32. The inductive coupling device of claim 18, wherein a first pair of sensors of the plurality of sensors is positioned on the coil to monitor bending of the coil in a first direction.

33. The inductive coupling device of claim 32, wherein a second pair of sensors of the plurality of sensors is positioned on the coil to monitor bending of the coil in a second direction that is different from the first direction.

* * * * *